United States Patent [19]
Kanda et al.

[11] Patent Number: 5,683,964
[45] Date of Patent: Nov. 4, 1997

[54] N-(SUBSTITUTED AMINO)IMIDE DERIVATIVES, PREPARATION PROCESS THEREOF, AND HERBICIDAL COMPOSITION

[75] Inventors: Yoichi Kanda; Hideo Arabori; Masato Arahira; Tsutomu Sato, all of Iwaki, Japan

[73] Assignee: Kureha Kagaku Kogyo K.K., Tokyo, Japan

[21] Appl. No.: 504,862

[22] Filed: Jul. 20, 1995

[30] Foreign Application Priority Data

Jul. 20, 1994 [JP] Japan .................. 6-190089

[51] Int. Cl.⁶ .................. A01N 43/54; A01N 43/66; A01N 43/68; C07D 251/42
[52] U.S. Cl. .................. 504/213; 504/215; 544/198; 544/209; 544/212; 544/321; 544/324; 544/331; 544/332
[58] Field of Search .................. 544/198, 209, 544/212, 321, 324, 331, 332; 504/213, 215

[56] References Cited

U.S. PATENT DOCUMENTS

| | | | |
|---|---|---|---|
| 4,169,719 | 10/1979 | Levitt | 504/214 |
| 4,440,565 | 4/1984 | Willms et al. | 504/212 |
| 4,473,394 | 9/1984 | Budzinski | 504/213 |
| 4,515,620 | 5/1985 | Boehner | 504/212 |
| 4,601,747 | 7/1986 | Willms et al. | 504/214 |
| 4,718,937 | 1/1988 | Willms et al. | 504/212 |

FOREIGN PATENT DOCUMENTS

| | | |
|---|---|---|
| 51 466 | 10/1981 | European Pat. Off. |
| 98 569 | 7/1983 | European Pat. Off. |
| 2 015 503 | 3/1979 | United Kingdom . |
| 2 110 689 | 12/1982 | United Kingdom . |
| 93/24482 | 12/1993 | WIPO . |

*Primary Examiner*—Richard L. Raymond
*Attorney, Agent, or Firm*—Lowe, Price, LeBlanc & Becker

[57] ABSTRACT

An N-(substituted amino)imide derivative represented by the formula (I) is a novel compound which can be utilized as an effective ingredient of herbicidal compositions.

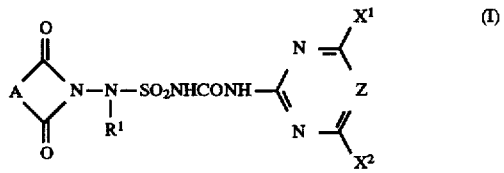

wherein, $R^1$ is hydrogen atom, $C_1$–$C_4$ alkyl group, $C_7$–$C_9$ aralkyl group, $C_1$–$C_4$ haloalkyl group, ($C_1$–$C_4$ alkyl) carbonyl group or ($C_1$–$C_4$ alkyl)sulfonyl group;

A represents a structure selected from the group consisting of the following formulas (A-1), (A-2), (A-3), (A-4) and (A-5)

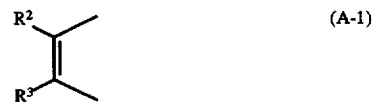

(A-1)

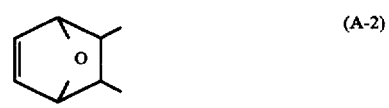

(A-2)

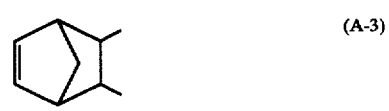

(A-3)

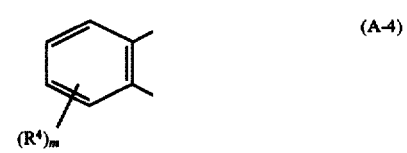

(A-4)

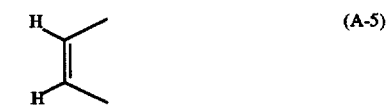

(A-5)

wherein $R^2$ and $R^3$ in the formula (A-1) are independently hydrogen atom or $C_1$–$C_4$ alkyl group, but not $R^2=R^3=H$, $R^4$ in the formula (A-4) is halogen atom, $C_1$–$C_4$ alkyl group and/or nitro group, m is an integer of 0–4, the substituents of m not less than 2 being same or different;

$X^1$ and $X^2$ are independently hydrogen atom, halogen atom, $C_1$–$C_4$ alkyl group, $C_1$–$C_4$ alkoxy group, $C_1$–$C_4$ alkylthio group, $C_1$–$C_4$ haloalkyl group, $C_1$–$C_4$ haloalkoxy group, $C_1$–$C_4$ haloalkylthio group, $C_2$–$C_4$ alkoxyalkyl group, $C_2$–$C_4$ thioalkoxyalkyl group or $NR^7R^8$, wherein $R^7$ and $R^8$ are independently hydrogen atom, $C_1$–$C_4$ alkyl group or $C_1$–$C_4$ alkoxy group; and Z is nitrogen atom or CH.

7 Claims, No Drawings

N-(SUBSTITUTED AMINO)IMIDE DERIVATIVES, PREPARATION PROCESS THEREOF, AND HERBICIDAL COMPOSITION

BACKGROUND OF THE INVENTION

1. Field of the Invention

The present invention relates to N-(substituted amino) imide derivatives, production process thereof, and 4herbicides containing the derivatives as active ingredients.

2. Description of the Related Arts

Regarding herbicidal compounds having an (azinylureylene)sulfonyl group such as a {[(pyrimidin-2-yl- or 1,3,5-triazin-2-yl)aminocarbonyl]aminosulfonyl} group, a variety of compounds has heretofore been reported. For example, there are following reports regarding atoms to which an (azinylureylene)sulfonyl group is attached.

U.S. Pat. No. 4,169,719: Carbon atoms in a nonsubstituted or substituted benzene ring.

EP-A-51466: α-Carbon atom in the unsubstituted or substituted toluene.

U.S. Pat. No. 4,473,394: Carbon atom in the unsubstituted or substituted pyrrole ring.

GB 2,015,503 and EP-A-98569: Oxygen atom of hydroxyl group in unsubstituted or substituted phenols.

U.S. Pat. No. 4,440,565: Oxygen atom of hydroxyl group in unsubstituted or substituted alcohols.

U.S. Pat. No. 4,601,747 and U.S. Pat. No. 4,718,937: Nitrogen atom of the alkanesulfonamide group or alkoxyamino group.

U.S. Pat. No. 4,515,620: Nitrogen atom of the amino group in substituted anilines or 1-aminoindanes.

GB Patent 2,110,689: Nitrogen atom in the ring of pyrrolidine, piperidine, morpholine, thiomorpholine or 1,3-thiazolidine.

Among herbicidal compounds described in the above patent publications, compounds having an (azinylureylene) sulfonyl group such as {[(pyrimidin-2-yl-or 1,3,5-triazin-2-yl)aminocarbonyl]aminosulfonyl} group on a nitrogen atom of the nitrogen containing heterocyclic ring have been known (GB 2,110,689), but compounds having an (azinylureylene)sulfonyl group which is attached to a nitrogen atom of the imide group through another nitrogen atom have not be known.

By the way, there have conventionally been strong demands for herbicides capable of exhibiting reliable herbicidal activity even at such low application dosages as bringing about the advantage of reducing the amount present in the environment, herbicides capable of exhibiting selectivity between crops and weeds irrespective of variations in environmental conditions, herbicides free from crop injury to the second crop in double cropping, etc.

The present invention has been completed with a view toward meeting such demands.

Thus the present inventors have found that compounds having an (azinylureylene)sulfonyl group which is attached to a nitrogen atom of the imide group through another nitrogen atom have excellent herbicidal activity, leading to the completion of the present invention.

SUMMARY OF THE INVENTION

Therefore, an object of the present invention is to provide novel compounds exhibiting excellent herbicidal activity, to provide a preparation process thereof, to provide novel herbicidal compositions containing one or more of the derivatives as active ingredients, and to intermediate compounds thereof.

The present invention has the following constructive features.

In the first aspect of the invention, there is thus provided an N-(substituted amino)imide derivative represented by the formula (I).

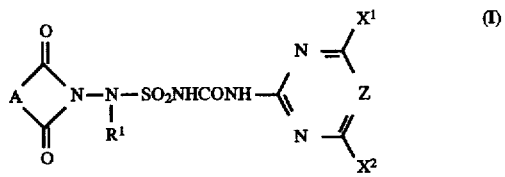

wherein, $R^1$ is hydrogen atom, $C_1$-$C_4$ alkyl group, $C_7$-$C_9$ aralkyl group, $C_1$-$C_4$ haloalkyl group, ($C_1$-$C_4$ alkyl) carbonyl group or ($C_1$-$C_4$ alkyl)sulfonyl group;

A represents a structure selected from the group consisting of the following formulas (A-1), (A-2), (A-3), (A-4) and (A-5)

wherein $R^2$ and $R^3$ in the formula (A-1) are independently hydrogen atom or $C_1$-$C_4$ alkyl group, but not $R^2$=$R^3$=H, $R^4$ in the formula (A-4) is halogen atom, $C_1$-$C_4$ alkyl group and/or nitro group, m is an integer of 0-4, the substituents of m not less than 2 being same or different;

$X^1$ and $X^2$ are independently hydrogen atom, halogen atom, $C_1$-$C_4$ alkyl group, $C_1$-$C_4$ alkoxy group, $C_1$-$C_4$ alkylthio group, $C_1$-$C_4$ haloalkyl group, $C_1$-$C_4$ haloalkoxy group, $C_1$-$C_4$ haloalkylthio group, $C_2$-$C_4$ alkoxyalkyl group, $C_2$-$C_4$ thioalkoxyalkyl group or $NR^7R^8$, wherein $R^7$ and $R^8$ are independently hydrogen atom, $C_1$-$C_4$ alkyl group or $C_1$-$C_4$ alkoxy group; and Z is nitrogen atom or CH.

In the second aspect of the invention, there is provided a process for preparation of the above N-(substituted amino) imide derivative represented by the formula (I-a), which comprises reacting an N-aminoimide derivative of the formula (II-a) with an (azinylureylene)sulfonyl halide of the formula (III):

according to the following reaction formula:

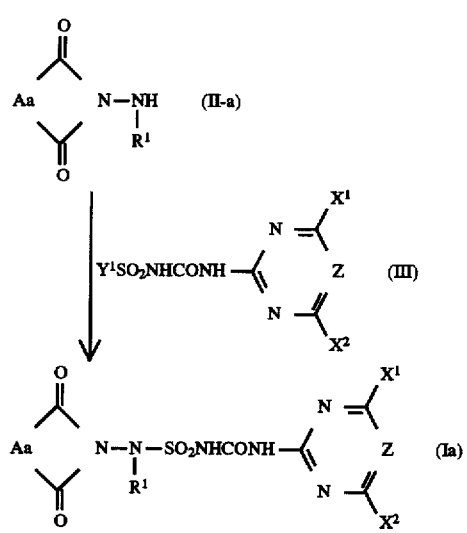

wherein Aa is a structure selected from the group consisting of the above-mentioned formulas (A-1), (A-2), (A-3) and (A-4), $X^1$, $X^2$ and Z have each the same meaning as defined above, and $y_1$ is halogen atom.

In the third aspect of the invention, there is provided a process for preparation of an N-(substituted amino)imide derivative represented by the formula (I-b1), which comprises reacting an N-(substituted amino)imide derivative of the formula (I-b2) with a compound represented by the formula (IV) in the presence of a base to replace the hydrogen atom on N-amino group with $R^1b$ according to the following reaction formula:

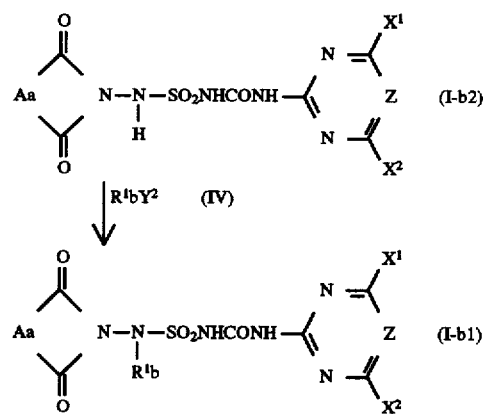

wherein Aa is a structure selected from the group consisting of the above-mentioned formulas (A-1), (A-2), (A-3) and (A-4), $X^1$, $X^2$, Z and m have each the same meaning as defined above, $R^1b$ is $C_1$–$C_4$ alkyl group, $C_7$–$C_9$ aralkyl group, $C_1$–$C_4$ haloalkyl group, ($C_1$–$C_4$ alkyl)carbonyl group or ($C_1$–$C_4$ alkyl)sulfonyl group, and $y_2$ is halogen atom or [($C_1$–$C_4$ alkyl)carbonyl]oxy group.

In the fourth aspect of the invention, there is provided a process for preparation of an N-(substituted amino)imide derivative of the formula (I-c1), which comprises pyrolysis of an N-(substituted amino)imide derivative of the formula (I-c2) according to the following reaction formula:

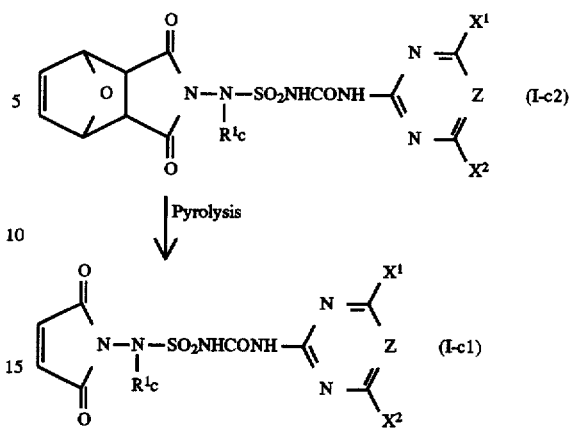

wherein $R^1c$ is $C_1$–$C_4$ alkyl group, $C_7$–$C_9$ aralkyl group or $C_1$–$C_4$ haloalkyl group, $X^1$, $X^2$ and Z have each the same meaning as defined above.

In the fifth aspect of the invention, there is provided a herbicidal agent which comprises a herbicidally effective amount of an N-(substituted amino)imide derivative of the above-mentioned formula (I) as an active ingredient.

DETAILED DESCRIPTION OF PREFERRED EMBODIMENTS

In the description hereinafter, A, Aa, A-1- A-5, $R^1$–$R^4$, $R^1b$, $R^1c$, $X^1$, $X^2$, Z m, $y_1$ and $y_2$ in the above formulas have each the same meaning as defined above. $C_1$–$C_4$ alkyl in $R^2$ and $R^3$ includes methyl and ethyl. Halogen in $R^4$ includes fluorine, chlorine, bromine and idodine. $C_1$–$C_4$ alkyl in $R^4$ includes methyl and ethyl.

Specific examples of the derivatives of the above formula (I) according to the present invention include those shown in Table 1-Table 9. In the tables, $CH_2Ph$ means benzyl group.

TABLE 1

| No. | A | $R^1$ | $X^1$ | $X^2$ | Z |
|---|---|---|---|---|---|
| I-1 | In compounds | H | $CF_3$ | $OCH_3$ | CH |
| I-2 | No. I-1- | H | $CF_3$ | $OCHF_2$ | CH |
| I-3 | No. I-168, | H | $CH(CH_3)_2$ | $OCH_3$ | CH |
| I-4 | the group A is | H | $CH(OCH_3)_2$ | $CH_3$ | CH |
| I-5 | A-1($R^2 = R^3 =$ | H | $CH_2F$ | $OCH_3$ | CH |
| I-6 | $CH_3$) | H | $CH_2F$ | $OCHF_2$ | CH |
| I-7 |  | H | $CH_2OCH_3$ | $CH_3$ | CH |
| I-11 |  | H | $CH_2OCH_3$ | $OCH_3$ | CH |
| I-12 |  | H | $CH_2OCH_3$ | $OCHF_2$ | CH |
| I-13 |  | H | $CH_3$ | $CF_3$ | CH |
| I-14 |  | H | $CH_3$ | $CH_3$ | CH |
| I-15 |  | H | $CH_3$ | Cl | CH |
| I-16 |  | H | $CH_3$ | F | CH |
| I-17 |  | H | $CH_3$ | H | CH |
| I-21 |  | H | $CH_3$ | $OC_2H_5$ | CH |
| I-22 |  | H | $CH_3$ | $OCF_2CHF_2$ | CH |
| I-23 |  | H | $CH_3$ | $OCF_2CHFCF_3$ | CH |
| I-24 |  | H | $CH_3$ | $OCH_2CF_3$ | CH |
| I-25 |  | H | $CH_3$ | $OCH_2CH_2F$ | CH |
| I-26 |  | H | $CH_3$ | $OCH_2CHF_2$ | CH |
| I-27 |  | H | $CH_3$ | $OCH_3$ | CH |
| I-31 |  | H | $CH_3$ | $OCHF_2$ | CH |
| I-32 |  | H | $CH_3$ | $SCH_3$ | CH |
| I-33 |  | H | $CHF_2$ | $CH_3$ | CH |
| I-34 |  | H | Cl | Cl | CH |
| I-35 |  | H | Cl | H | CH |
| I-36 |  | H | Cl | $N(CH_3)_2$ | CH |
| I-37 |  | H | Cl | $NH_2$ | CH |
| I-41 |  | H | Cl | $OC_2H_5$ | CH |

TABLE 1-continued

| No. | A | R¹ | X¹ | X² | Z |
|---|---|---|---|---|---|
| I-42 | | H | Cl | $OCF_2CHF_2$ | CH |
| I-43 | | H | Cl | $OCF_2CHFCl$ | CH |
| I-44 | | H | Cl | $OCH_3$ | CH |
| I-45 | | H | Cl | $OCHF_2$ | CH |
| I-46 | | H | $N(CH_3)_2$ | $OCF_2CHF_2$ | CH |
| I-47 | | H | $N(CH_3)_2$ | $OCH_3$ | CH |
| I-51 | | H | $N(CH_3)_2$ | $OCHF_2$ | CH |
| I-52 | | H | $N(CH_3)_2$ | $SCHF_2$ | CH |
| I-53 | | H | $N(CH_3)C_2H_5$ | $OCHF_2$ | CH |
| I-54 | | H | $N(CH_3)OCH_3$ | $OCHF_2$ | CH |
| I-55 | | H | $NH_2$ | $OCH_3$ | CH |
| I-56 | | H | $NHCH_3$ | $OCH_3$ | CH |
| I-57 | | H | $NHCH_3$ | $OCHF_2$ | CH |
| I-61 | | H | $OC_2H_5$ | $OC_2H_5$ | CH |
| I-62 | | H | $OCF_2CHF_2$ | $SCH_3$ | CH |
| I-63 | | H | $OCH(CH_3)_2$ | $OCHF_2$ | CH |
| I-64 | | H | $OCH_2CF_3$ | $OCH_3$ | CH |
| I-65 | | H | $OCH_2CH_2F$ | $OCH_3$ | CH |
| I-66 | | H | $OCH_2CHF_2$ | $OCH_3$ | CH |
| I-67 | | H | $OCH_3$ | $OC_2H_5$ | CH |
| I-71 | | H | $OCH_3$ | $OCF_2CHF_2$ | CH |
| I-72 | | H | $OCH_3$ | $OCF_2CHFCF_3$ | CH |
| I-73 | | H | $OCH_3$ | $OCH(CH_3)_2$ | CH |
| I-74 | | H | $OCH_3$ | $OCH_3$ | CH |
| I-75 | | H | $OCH_3$ | $SCH_3$ | CH |
| I-76 | | H | $OCH_3$ | $SCHF_2$ | CH |
| I-77 | | H | $OCHF_2$ | $OCH_2CF_3$ | CH |
| I-81 | | H | $OCHF_2$ | $OCH_2CH_3$ | CH |
| I-82 | | H | $OCHF_2$ | $OCH_3$ | CH |
| I-83 | | H | $OCHF_2$ | $OCHF_2$ | CH |
| I-84 | | H | $OCHF_2$ | $SCH_3$ | CH |
| I-85 | | H | $C_2H_5$ | $OCH_3$ | N |
| I-86 | | H | $C_2H_5$ | $SCH_3$ | N |
| I-87 | | H | $CF_3$ | $OCH_3$ | N |
| I-91 | | H | $CH(CH_3)_2$ | $CH_3$ | N |
| I-92 | | H | $CH(CH_3)_2$ | Cl | N |
| I-93 | | H | $CH(CH_3)_2$ | $OCH_3$ | N |
| I-94 | | H | $CH(CH_3)_2$ | $SCH_3$ | N |
| I-95 | | H | $CH_2CF_3$ | $CH_3$ | N |
| I-96 | | H | $CH_2F$ | $CH_3$ | N |
| I-97 | | H | $CH_2F$ | $OCH_3$ | N |
| I-101 | | H | $CH_2OCH_3$ | $CH_3$ | N |
| I-102 | | H | $CH_2OCH_3$ | $OCH_3$ | N |
| I-103 | | H | $CH_2SCH_3$ | $CH_3$ | N |
| I-104 | | H | $CH_2SCH_3$ | Cl | N |
| I-105 | | H | $CH_2SCH_3$ | $OC_2H_5$ | N |
| I-106 | | H | $CH_2SCH_3$ | $OCH_3$ | N |
| I-107 | | H | $CH_2SCH_3$ | $SCH_3$ | N |
| I-111 | | H | $CH_3$ | $CF_3$ | N |
| I-112 | | H | $CH_3$ | $CH_3$ | N |
| I-113 | | H | $CH_3$ | Cl | N |
| I-114 | | H | $CH_3$ | F | N |
| I-115 | | H | $CH_3$ | H | N |
| I-116 | | H | $CH_3$ | $OCH_2CF_3$ | N |
| I-117 | | H | $CH_3$ | $OCH_2CH_2F$ | N |
| I-121 | | H | $CH_3$ | $OCH_2CHF_2$ | N |
| I-122 | | H | $CH_3$ | $OCH_3$ | N |
| I-123 | | H | $CH_3$ | $SCH_3$ | N |
| I-124 | | H | $CH_3$ | $SCHF_2$ | N |
| I-125 | | H | $CHF_2$ | $CH_3$ | N |
| I-126 | | H | $CHF_2$ | $OCH_3$ | N |
| I-127 | | H | Cl | Cl | N |
| I-131 | | H | Cl | $OCH(CH_3)_2$ | N |
| I-132 | | H | Cl | $OCH_2CF_3$ | N |
| I-133 | | H | Cl | $OCH_3$ | N |
| I-134 | | H | Cl | $SCH_3$ | N |
| I-135 | | H | F | $OCH_3$ | N |
| I-136 | | H | H | $NH(CH_3)$ | N |
| I-137 | | H | $N(CH_3)_2$ | $OCH_3$ | N |
| I-141 | | H | $N(CH_3)_2$ | $SCHF_2$ | N |
| I-142 | | H | $NHCH_3$ | $OCH_3$ | N |
| I-143 | | H | $OC_2H_5$ | $OC_2H_5$ | N |
| I-144 | | H | $OCF_2CHF_2$ | $SCH_3$ | N |
| I-145 | | H | $OCF_2CHFBr$ | $SCH_3$ | N |
| I-146 | | H | $OCF_2CHFCF_3$ | $SCH_3$ | N |
| I-147 | | H | $OCH(CH_3)_2$ | $OCH_3$ | N |
| I-151 | | H | $OCH(CH_3)_2$ | $SCH_3$ | N |
| I-152 | | H | $OCH(CH_3)CH_2CH_3$ | $OCH_3$ | N |
| I-153 | | H | $OCH_2CF_3$ | $OCF_2CHF_2$ | N |
| I-154 | | H | $OCH_2CF_3$ | $OCH_3$ | N |
| I-155 | | H | $OCH_2CHF_2$ | $OCH_3$ | N |
| I-156 | | H | $OCH_3$ | $OC_2H_5$ | N |
| I-157 | | H | $OCH_3$ | $OCF_2CHF_2$ | N |
| I-161 | | H | $OCH_3$ | $OCF_2CHFBr$ | N |
| I-162 | | H | $OCH_3$ | $OCF_2CHFCF_3$ | N |
| I-163 | | H | $OCH_3$ | $OCF_2CHFCl$ | N |
| I-164 | | H | $OCH_3$ | $OCH_3$ | N |
| I-165 | | H | $OCH_3$ | $OCHF_2$ | N |
| I-166 | | H | $OCH_3$ | $SCH(CH_3)_2$ | N |
| I-167 | | H | $OCH_3$ | $SCH_3$ | N |
| I-168 | | H | $OCH_3$ | $SCHF_2$ | N |

TABLE 2

| No. | A | R¹ | X¹ | X² | Z |
|---|---|---|---|---|---|
| I-171 | In compounds | CH3 | $CF_3$ | $OCH_3$ | CH |
| I-172 | No. I-171– | CH3 | $CF_3$ | $OCHF_2$ | CH |
| I-173 | No. I-338, | CH3 | $CH(CH_3)_2$ | $OCH_3$ | CH |
| I-174 | the group A is | CH3 | $CH(OCH_3)_2$ | $CH_3$ | CH |
| I-175 | A-1($R^2 = R^3 =$ | CH3 | $CH_2F$ | $OCH_3$ | CH |
| I-176 | $CH_3$) | CH3 | $CH_2F$ | $OCHF_2$ | CH |
| I-177 | | CH3 | $CH_2OCH_3$ | $CH_3$ | CH |
| I-181 | | CH3 | $CH_2OCH_3$ | $OCH_3$ | CH |
| I-182 | | CH3 | $CH_2OCH_3$ | $OCHF_2$ | CH |
| I-183 | | CH3 | $CH_3$ | $CF_3$ | CH |
| I-184 | | CH3 | $CH_3$ | $CH_3$ | CH |
| I-185 | | CH3 | $CH_3$ | Cl | CH |
| I-186 | | $CH_3$ | $CH_3$ | F | CH |
| I-187 | | $CH_3$ | $CH_3$ | H | CH |
| I-191 | | $CH_3$ | $CH_3$ | $OC_2H_5$ | CH |
| I-192 | | $CH_3$ | $CH_3$ | $OCF_2CHF_2$ | CH |
| I-193 | | $CH_3$ | $CH_3$ | $OCF_2CHFCF_3$ | CH |
| I-194 | | $CH_3$ | $CH_3$ | $OCH_2CF_3$ | CH |
| I-195 | | $CH_3$ | $CH_3$ | $OCH_2CH_2F$ | CH |
| I-196 | | $CH_3$ | $CH_3$ | $OCH_2CHF_2$ | CH |
| I-197 | | $CH_3$ | $CH_3$ | $OCH_3$ | CH |
| I-201 | | $CH_3$ | $CH_3$ | $OCHF_2$ | CH |
| I-202 | | $CH_3$ | $CH_3$ | $SCH_3$ | CH |
| I-203 | | $CH_3$ | $CHF_2$ | $CH_3$ | CH |
| I-204 | | $CH_3$ | Cl | Cl | CH |
| I-205 | | $CH_3$ | Cl | H | CH |
| I-206 | | $CH_3$ | Cl | $N(CH_3)_2$ | CH |
| I-207 | | $CH_3$ | Cl | $NH_2$ | CH |
| I-211 | | $CH_3$ | Cl | $OC_2H_5$ | CH |
| I-212 | | $CH_3$ | Cl | $OCF_2CHF_2$ | CH |
| I-213 | | $CH_3$ | Cl | $OCF_2CHFCl$ | CH |
| I-214 | | $CH_3$ | Cl | $OCH_3$ | CH |
| I-215 | | $CH_3$ | Cl | $OCHF_2$ | CH |
| I-216 | | $CH_3$ | $N(CH_3)_2$ | $OCF_2CHF_2$ | CH |
| I-217 | | $CH_3$ | $N(CH_3)_2$ | $OCH_3$ | CH |
| I-221 | | $CH_3$ | $N(CH_3)_2$ | $OCHF_2$ | CH |
| I-222 | | $CH_3$ | $N(CH_3)_2$ | $SCHF_2$ | CH |
| I-223 | | $CH_3$ | $N(CH_3)C_2H_5$ | $OCHF_2$ | CH |
| I-224 | | $CH_3$ | $N(CH_3)OCH_3$ | $OCHF_2$ | CH |
| I-225 | | $CH_3$ | $NH_2$ | $OCH_3$ | CH |
| I-226 | | $CH_3$ | $NHCH_3$ | $OCH_3$ | CH |
| I-227 | | $CH_3$ | $NHCH_3$ | $OCHF_2$ | CH |
| I-231 | | $CH_3$ | $OC_2H_5$ | $OC_2H_5$ | CH |
| I-232 | | $CH_3$ | $OCF_2CHF_2$ | $SCH_3$ | CH |
| I-233 | | $CH_3$ | $OCH(CH_3)_2$ | $OCHF_2$ | CH |
| I-234 | | $CH_3$ | $OCH_2CF_3$ | $OCH_3$ | CH |
| I-235 | | $CH_3$ | $OCH_2CH_2F$ | $OCH_3$ | CH |
| I-236 | | $CH_3$ | $OCH_2CHF_2$ | $OCH_3$ | CH |
| I-237 | | $CH_3$ | $OCH_3$ | $OC_2H_5$ | CH |
| I-241 | | $CH_3$ | $OCH_3$ | $OCF_2CHF_2$ | CH |
| I-242 | | $CH_3$ | $OCH_3$ | $OCF_2CHFCF_3$ | CH |
| I-243 | | $CH_3$ | $OCH_3$ | $OCH(CH_3)_2$ | CH |
| I-244 | | $CH_3$ | $OCH_3$ | $OCH_3$ | CH |
| I-245 | | $CH_3$ | $OCH_3$ | $SCH_3$ | CH |
| I-246 | | $CH_3$ | $OCH_3$ | $SCHF_2$ | CH |

TABLE 2-continued

| No. | A | R¹ | X¹ | X² | Z |
|---|---|---|---|---|---|
| I-247 | | $CH_3$ | $OCHF_2$ | $OCH_2CF_3$ | CH |
| I-251 | | $CH_3$ | $OCHF_2$ | $OCH_2CH_3$ | CH |
| I-252 | | $CH_3$ | $OCHF_2$ | $OCH_3$ | CH |
| I-253 | | $CH_3$ | $OCHF_2$ | $OCHF_2$ | CH |
| I-254 | | $CH_3$ | $OCHF_2$ | $SCH_3$ | CH |
| I-255 | | $CH_3$ | $C_2H_5$ | $OCH_3$ | N |
| I-256 | | $CH_3$ | $C_2H_5$ | $SCH_3$ | N |
| I-257 | | $CH_3$ | $CF_3$ | $OCH_3$ | N |
| I-261 | | $CH_3$ | $CH(CH_3)_2$ | $CH_3$ | N |
| I-262 | | $CH_3$ | $CH(CH_3)_2$ | Cl | N |
| I-263 | | $CH_3$ | $CH(CH_3)_2$ | $OCH_3$ | N |
| I-264 | | $CH_3$ | $CH(CH_3)_2$ | $SCH_3$ | N |
| I-265 | | $CH_3$ | $CH_2CF_3$ | $CH_3$ | N |
| I-266 | | $CH_3$ | $CH_2F$ | $CH_3$ | N |
| I-267 | | $CH_3$ | $CH_2F$ | $OCH_3$ | N |
| I-271 | | $CH_3$ | $CH_2OCH_3$ | $CH_3$ | N |
| I-272 | | $CH_3$ | $CH_2OCH_3$ | $OCH_3$ | N |
| I-273 | | $CH_3$ | $CH_2SCH_3$ | $CH_3$ | N |
| I-274 | | $CH_3$ | $CH_2SCH_3$ | Cl | N |
| I-275 | | $CH_3$ | $CH_2SCH_3$ | $OC_2H_5$ | N |
| I-276 | | $CH_3$ | $CH_2SCH_3$ | $OCH_3$ | N |
| I-277 | | $CH_3$ | $CH_2SCH_3$ | $SCH_3$ | N |
| I-281 | | $CH_3$ | $CH_3$ | $CF_3$ | N |
| I-282 | | $CH_3$ | $CH_3$ | $CH_3$ | N |
| I-283 | | $CH_3$ | $CH_3$ | Cl | N |
| I-284 | | $CH_3$ | $CH_3$ | F | N |
| I-285 | | $CH_3$ | $CH_3$ | H | N |
| I-286 | | $CH_3$ | $CH_3$ | $OCH_2CF_3$ | N |
| I-287 | | $CH_3$ | $CH_3$ | $OCH_2CH_2F$ | N |
| I-291 | | $CH_3$ | $CH_3$ | $OCH_2CHF_2$ | N |
| I-292 | | $CH_3$ | $CH_3$ | $OCH_3$ | N |
| I-293 | | $CH_3$ | $CH_3$ | $SCH_3$ | N |
| I-294 | | $CH_3$ | $CH_3$ | $SCHF_2$ | N |
| I-295 | | $CH_3$ | $CHF_2$ | $CH_3$ | N |
| I-296 | | $CH_3$ | $CHF_2$ | $OCH_3$ | N |
| I-297 | | $CH_3$ | Cl | Cl | N |
| I-301 | | $CH_3$ | Cl | $OCH(CH_3)_2$ | N |
| I-302 | | $CH_3$ | Cl | $OCH_2CF_3$ | N |
| I-303 | | $CH_3$ | Cl | $OCH_3$ | N |
| I-304 | | $CH_3$ | Cl | $SCH_3$ | N |
| I-305 | | $CH_3$ | F | $OCH_3$ | N |
| I-306 | | $CH_3$ | H | $NH(CH_3)$ | N |
| I-307 | | $CH_3$ | $N(CH_3)_2$ | $OCH_3$ | N |
| I-311 | | $CH_3$ | $N(CH_3)_2$ | $SCHF_2$ | N |
| I-312 | | $CH_3$ | $NHCH_3$ | $OCH_3$ | N |
| I-313 | | $CH_3$ | $OC_2H_5$ | $OC2H_5$ | N |
| I-314 | | $CH_3$ | $OCF_2CHF_2$ | $SCH_3$ | N |
| I-315 | | $CH_3$ | $OCF_2CHFBr$ | $SCH_3$ | N |
| I-316 | | $CH_3$ | $OCF_2CHFCF_3$ | $SCH_3$ | N |
| I-317 | | $CH_3$ | $OCH(CH_3)_2$ | $OCH_3$ | N |
| I-321 | | $CH_3$ | $OCH(CH_3)_2$ | $SCH_3$ | N |
| I-322 | | $CH_3$ | $OCH(CH_3)CH2CH_3$ | $OCH_3$ | N |
| I-323 | | $CH_3$ | $OCH_2CF_3$ | $OCF_2CHF_2$ | N |
| I-324 | | $CH_3$ | $OCH_2CF_3$ | $OCH_3$ | N |
| I-325 | | $CH_3$ | $OCH_2CHF_2$ | $OCH_3$ | N |
| I-326 | | $CH_3$ | $OCH_3$ | $O_2H_5$ | N |
| I-327 | | $CH_3$ | $OCH_3$ | $OCF_2CHF_2$ | N |
| I-331 | | $CH_3$ | $OCH_3$ | $OCF_2CHFBr$ | N |
| I-332 | | $CH_3$ | $OCH_3$ | $OCF_2CHFCF_3$ | N |
| I-333 | | $CH_3$ | $OCH_3$ | $OCF_2CHFCl$ | N |
| I-334 | | $CH_3$ | $OCH_3$ | $OCF_3$ | N |
| I-335 | | $CH_3$ | $OCH_3$ | $OCHF_2$ | N |
| I-336 | | $CH_3$ | $OCH_3$ | $SCH(CH_3)_2$ | N |
| I-337 | | $CH_3$ | $OCH_3$ | $SCH_3$ | N |
| I-338 | | $CH_3$ | $OCH_3$ | $SCHF_2$ | N |

TABLE 3

| No. | A | R¹ | X¹ | X² | Z |
|---|---|---|---|---|---|
| I-341 | In compounds | $CH_2Ph$ | $CH_3$ | $CH_3$ | CH |
| I-342 | No. I-341– | | $CH_3$ | Cl | CH |
| I-343 | No. I-357, | | $CH_3$ | $OCH_3$ | CH |
| I-344 | the group A is | | Cl | Cl | CH |
| I-345 | A-1($R^2$=$R^3$=$CH_3$) | | Cl | $OCH_3$ | CH |
| I-346 | | | $OCH_3$ | $OCH_3$ | CH |
| I-347 | | | $CH_3$ | $CH_3$ | N |
| I-351 | | | $CH_3$ | Cl | N |
| I-352 | | | $CH_3$ | $OCH_3$ | N |
| I-353 | | | Cl | Cl | N |
| I-354 | | | Cl | $OCH_3$ | N |
| I-355 | | | $N(CH_3)_2$ | $OCH_3$ | N |
| I-356 | | | $OCH_2CH_2F$ | $OCH_3$ | N |
| I-357 | | | $OCH_3$ | $OCH_3$ | N |

TABLE 4

| No. | A | R¹ | X¹ | X² | Z |
|---|---|---|---|---|---|
| I-361 | In compounds | $COCH_3$ | $CH_3$ | CH | CH |
| I-362 | No. I-361– | | $CH_3$ | Cl | CH |
| I-363 | No. I-377, | | $CH_3$ | $OCH_3$ | CH |
| I-364 | the group A is | | Cl | Cl | CH |
| I-365 | A-1($R^2$=$R^3$=$CH_3$) | | Cl | $OCH_3$ | CH |
| I-366 | | | $OCH_3$ | $OCH_3$ | CH |
| I-367 | | | $CH_3$ | $CH_3$ | N |
| I-371 | | | $CH_3$ | Cl | N |
| I-372 | | | $CH_3$ | $OCH_3$ | N |
| I-373 | | | Cl | Cl | N |
| I-374 | | | Cl | $OCH_3$ | N |
| I-375 | | | $N(CH_3)_2$ | $OCH_3$ | N |
| I-376 | | | $OCH_2CH_2F$ | $OCH_3$ | N |
| I-377 | | | $OCH_3$ | $OCH_3$ | N |

TABLE 5

| No. | A | R¹ | X¹ | X² | Z |
|---|---|---|---|---|---|
| I-381 | In compounds | $SO_2CH_3$ | $CH_3$ | $CH_3$ | CH |
| I-382 | No. I-381– | | $CH_3$ | Cl | CH |
| I-383 | No. I-397, | | $CH_3$ | $OCH_3$ | CH |
| I-384 | the group A is | | Cl | Cl | CH |
| I-385 | A-1($R^2$=$R^3$=$CH_3$) | Cl | $OCH_3$ | CH | |
| I-386 | | | $OCH_3$ | $OCH_3$ | CH |
| I-387 | | | $CH_3$ | $CH_3$ | N |
| I-391 | | | $CH_3$ | Cl | N |
| I-392 | | | $CH_3$ | $OCH_3$ | N |
| I-393 | | | Cl | Cl | N |
| I-394 | | | Cl | $OCH_3$ | N |
| I-395 | | | $N(CH_3)_2$ | $OCH_3$ | N |
| I-396 | | | $OCH_2CH_2F$ | $OCH_3$ | N |
| I-397 | | | $OCH_3$ | $OCH_3$ | N |

TABLE 6

| No. | A | R¹ | X¹ | X² | Z |
|---|---|---|---|---|---|
| I-401 | In compounds | $CH_3$ | $CF_3$ | $OCH_3$ | CH |
| I-402 | No. I-401– | $CH_3$ | $CF_3$ | $OCHF_2$ | CH |
| I-403 | No. I-568, | $CH_3$ | $CH(CH_3)_2$ | $OCH_3$ | CH |
| I-404 | the group A is | $CH_3$ | $CH(OCH_3)_2$ | $CH_3$ | CH |
| I-405 | A-5 | $CH_3$ | $CH_2F$ | $OCH_3$ | CH |
| I-406 | | $CH_3$ | $CH_2F$ | $OCHF_2$ | CH |
| I-407 | | $CH_3$ | $CH_2OCH_3$ | $CH_3$ | CH |
| I-411 | | $CH_3$ | $CH_2OCH_3$ | $OCH_3$ | CH |
| I-412 | | $CH_3$ | $CH_2OCH_3$ | $OCHF_2$ | CH |
| I-413 | | $CH_3$ | $CH_3$ | $CF_3$ | CH |
| I-414 | | $CH_3$ | $CH_3$ | $CH_3$ | CH |
| I-415 | | $CH_3$ | $CH_3$ | Cl | CH |
| I-416 | | $CH_3$ | $CH_3$ | F | CH |
| I-417 | | $CH_3$ | $CH_3$ | H | CH |
| I-421 | | $CH_3$ | $CH_3$ | $OC_2H_5$ | CH |
| I-422 | | $CH_3$ | $CH_3$ | $OCF_2CHF_2$ | CH |
| I-423 | | $CH_3$ | $CH_3$ | $OCF_2CHFCF_3$ | CH |

TABLE 6-continued

| No. | A | R¹ | X¹ | X² | Z |
|---|---|---|---|---|---|
| I-424 | | CH₃ | CH₃ | OCH₂CF₃ | CH |
| I-425 | | CH₃ | CH₃ | OCH₂CH₂F | CH |
| I-426 | | CH₃ | CH₃ | OCH₂CHF₂ | CH |
| I-427 | | CH₃ | CH₃ | OCH₃ | CH |
| I-431 | | CH₃ | CH₃ | OCHF₂ | CH |
| I-432 | | CH₃ | CH₃ | SCH₃ | CH |
| I-433 | | CH₃ | CHF₂ | CH₃ | CH |
| I-434 | | CH₃ | Cl | Cl | CH |
| I-435 | | CH₃ | Cl | H | CH |
| I-436 | | CH₃ | Cl | N(CH₃)₂ | CH |
| I-437 | | CH₃ | Cl | NH₂ | CH |
| I-441 | | CH₃ | Cl | OC₂H₅ | CH |
| I-442 | | CH₃ | Cl | OCF₂CHF₂ | CH |
| I-443 | | CH₃ | Cl | OCF₂CHFCl | CH |
| I-444 | | CH₃ | Cl | OCH₃ | CH |
| I-445 | | CH₃ | Cl | OCHF₃ | CH |
| I-446 | | CH₃ | N(CH₃)₂ | OCF₂CHF₂ | CH |
| I-447 | | CH₃ | N(CH₃)₂ | OCH₃ | CH |
| I-451 | | CH₃ | N(CH₃)₂ | OCHF₂ | CH |
| I-452 | | CH₃ | N(CH₃)₂ | SCHF₂ | CH |
| I-453 | | CH₃ | N(CH₃)C₂H₅ | OCHF₂ | CH |
| I-454 | | CH₃ | N(CH₃)OCH₃ | OCHF₂ | CH |
| I-455 | | CH₃ | NH₂ | OCH₃ | CH |
| I-456 | | CH₃ | NHCH₃ | OCH₃ | CH |
| I-457 | | CH₃ | NHCH₃ | OCHF₂ | CH |
| I-461 | | CH₃ | OC₂H₅ | OC₂H₅ | CH |
| I-462 | | CH₃ | OCF₂CHF₂ | SCH₃ | CH |
| I-463 | | CH₃ | OCH(CH₃)₂ | OCHF₂ | CH |
| I-464 | | CH₃ | OCH₂CF₃ | OCH₃ | CH |
| I-465 | | CH₃ | OCH₂CH₂F | OCH₃ | CH |
| I-466 | | CH₃ | OCH₂CHF₂ | OCH₃ | CH |
| I-467 | | CH₃ | OCH₃ | OC₂H₅ | CH |
| I-471 | | CH₃ | OCH₃ | OCF₂CHF₂ | CH |
| I-472 | | CH₃ | OCH₃ | OCF₂CHFCF₃ | CH |
| I-473 | | CH₃ | OCH₃ | OCH(CH₃)₂ | CH |
| I-474 | | CH₃ | OCH₃ | OCH₃ | CH |
| I-475 | | CH₃ | OCH₃ | SCH₃ | CH |
| I-476 | | CH₃ | OCH₃ | SCHF₂ | CH |
| I-477 | | CH₃ | OCHF₂ | OCH₂CF₃ | CH |
| I-481 | | CH₃ | OCHF₂ | OCH₂CH₃ | CH |
| I-482 | | CH₃ | OCHF₂ | OCH₃ | CH |
| I-483 | | CH₃ | OCHF₂ | OCHF₂ | CH |
| I-484 | | CH₃ | OCHF₂ | SCH₃ | CH |
| I-485 | | CH₃ | C₂H₅ | OCH₃ | N |
| I-486 | | CH₃ | C₂H₅ | SCH₃ | N |
| I-487 | | CH₃ | CF₃ | OCH₃ | N |
| I-491 | | CH₃ | CH(CH₃)₂ | CH₃ | N |
| I-492 | | CH₃ | CH(CH₃)₂ | Cl | N |
| I-493 | | CH₃ | CH(CH₃)₂ | OCH₃ | N |
| I-494 | | CH₃ | CH(CH₃)₂ | SCH₃ | N |
| I-495 | | CH₃ | CH₂CF₃ | CH₃ | N |
| I-496 | | CH₃ | CH₂F | CH₃ | N |
| I-497 | | CH₃ | CH₂F | OCH₃ | N |
| I-501 | | CH₃ | CH₂OCH₃ | CH₃ | N |
| I-502 | | CH₃ | CH₂OCH₃ | OCH₃ | N |
| I-503 | | CH₃ | CH₂SCH₃ | CH₃ | N |
| I-504 | | CH₃ | CH₂SCH₃ | Cl | N |
| I-505 | | CH₃ | CH₂SCH₃ | OC₂H₅ | N |
| I-506 | | CH₃ | CH₂SCH₃ | OCH₃ | N |
| I-507 | | CH₃ | CH₂SCH₃ | SCH₃ | N |
| I-511 | | CH₃ | CH₃ | CF₃ | N |
| I-512 | | CH₃ | CH₃ | CH₃ | N |
| I-513 | | CH₃ | CH₃ | Cl | N |
| I-514 | | CH₃ | CH₃ | F | N |
| I-515 | | CH₃ | CH₃ | H | N |
| I-516 | | CH₃ | CH₃ | OCH₂CF₃ | N |
| I-517 | | CH₃ | CH₃ | OCH₂CH₂F | N |
| I-521 | | CH₃ | CH₃ | OCH₂CHF₂ | N |
| I-522 | | CH₃ | CH₃ | OCH₃ | N |
| I-523 | | CH₃ | CH₃ | SCH₃ | N |
| I-524 | | CH₃ | CH₃ | SCHF₂ | N |
| I-525 | | CH₃ | CHF₂ | CH₃ | N |
| I-526 | | CH₃ | CHF₂ | OCH₃ | N |
| I-527 | | CH₃ | Cl | Cl | N |
| I-531 | | CH₃ | Cl | OCH(CH₃)₂ | N |
| I-532 | | CH₃ | Cl | OCH₂CF₃ | N |
| I-533 | | CH₃ | Cl | OCH₃ | N |
| I-534 | | CH₃ | Cl | SCH₃ | N |
| I-535 | | CH₃ | F | OCH₃ | N |
| I-536 | | CH₃ | H | NH(CH₃) | N |
| I-537 | | CH₃ | N(CH₃)₂ | OCH₃ | N |
| I-541 | | CH₃ | N(CH₃)₂ | SCHF₂ | N |
| I-542 | | CH₃ | NHCH₃ | OCH₃ | N |
| I-543 | | CH₃ | OC₂H₅ | OC₂H₅ | N |
| I-544 | | CH₃ | OCF₂CHF₂ | SCH₃ | N |
| I-545 | | CH₃ | OCF₂CHFBr | SCH₃ | N |
| I-546 | | CH₃ | OCF₂CHFCF₃ | SCH₃ | N |
| I-547 | | CH₃ | OCH(CH₃)₂ | OCH₃ | N |
| I-551 | | CH₃ | OCH(CH₃)₂ | SCH₃ | N |
| I-552 | | CH₃ | OCH(CH₃)CH₂CH₃ | OCH₃ | N |
| I-553 | | CH₃ | OCH₂CF₃ | OCF₂CHF₂ | N |
| I-554 | | CH₃ | OCH₂CF₃ | OCH₃ | N |
| I-555 | | CH₃ | OCH₂CHF₂ | OCH₃ | N |
| I-556 | | CH₃ | OCH₃ | OC₂H₅ | N |
| I-557 | | CH₃ | OCH₃ | OCF₂CHF₂ | N |
| I-561 | | CH₃ | OCH₃ | OCF₂CHFBr | N |
| I-562 | | CH₃ | OCH₃ | OCF₂CHFCF₃ | N |
| I-563 | | CH₃ | OCH₃ | OCF₂CHFCl | N |
| I-564 | | CH₃ | OCH₃ | OCH₃ | N |
| I-565 | | CH₃ | OCH₃ | OCHF₂ | N |
| I-566 | | CH₃ | OCH₃ | SCH(CH₃)₂ | N |
| I-567 | | CH₃ | OCH₃ | SCH₃ | N |
| I-568 | | CH₃ | OCH₃ | SCHF₂ | N |

TABLE 7

| No. | A | R¹ | X¹ | X² | Z |
|---|---|---|---|---|---|
| I-571 | In compounds | CH₃ | CF₃ | OCH₃ | CH |
| I-572 | No. I-571– | CH₃ | CF₃ | OCHF₂ | CH |
| I-573 | No. 1-738, | CH₃ | CH(CH₃)₂ | OCH₃ | CH |
| I-574 | the group A is | CH₃ | CH(OCH₃)₂ | CH₃ | CH |
| I-575 | A-2 | CH₃ | CH₂F | OCH₃ | CH |
| I-576 | | CH₃ | CH₂F | OCHF₂ | CH |
| I-577 | | CH₃ | CH₂OCH₃ | CH₃ | CH |
| I-581 | | CH₃ | CH₂OCH₃ | OCH₃ | CH |
| I-582 | | CH₃ | CH₂OCH₃ | OCHF₂ | CH |
| I-583 | | CH₃ | CH₃ | CF₃ | CH |
| I-584 | | CH₃ | CH₃ | CH₃ | CH |
| I-585 | | CH₃ | CH₃ | Cl | CH |
| I-586 | | CH₃ | CH₃ | F | CH |
| I-587 | | CH₃ | CH₃ | H | CH |
| I-591 | | CH₃ | CH₃ | OC₂H₅ | CH |
| I-592 | | CH₃ | CH₃ | OCF₂CHF₂ | CH |
| I-593 | | CH₃ | CH₃ | OCF₂CHFCF₃ | CH |
| I-594 | | CH₃ | CH₃ | OCH₂CF₃ | CH |
| I-595 | | CH₃ | CH₃ | OCH₂CH₂F | CH |
| I-596 | | CH₃ | CH₃ | OCH₂CHF₂ | CH |
| I-597 | | CH₃ | CH₃ | OCH₃ | CH |
| I-601 | | CH₃ | CH₃ | OCHF₂ | CH |
| I-602 | | CH₃ | CH₃ | SCH₃ | CH |
| I-603 | | CH₃ | CHF₂ | CH₃ | CH |
| I-604 | | CH₃ | Cl | Cl | CH |
| I-605 | | CH₃ | Cl | H | CH |
| I-606 | | CH₃ | Cl | N(CH₃)₂ | CH |
| I-607 | | CH₃ | Cl | NH₂ | CH |
| I-611 | | CH₃ | Cl | OC₂H₅ | CH |
| I-612 | | CH₃ | Cl | OCF₂CHF₂ | CH |
| I-613 | | CH₃ | Cl | OCF₂CHFCl | CH |
| I-614 | | CH₃ | Cl | OCH₃ | CH |
| I-615 | | CH₃ | Cl | OCHF₂ | CH |
| I-616 | | CH₃ | N(CH₃)₂ | OCF₂CHF₂ | CH |
| I-617 | | CH₃ | N(CH₃)₂ | OCH₃ | CH |
| I-621 | | CH₃ | N(CH₃)₂ | OCHF₂ | CH |
| I-622 | | CH₃ | N(CH₃)₂ | SCHF₂ | CH |
| I-623 | | CH₃ | N(CH₃)C₂H₅ | OCHF₂ | CH |
| I-624 | | CH₃ | N(CH₃)OCH₃ | OCHF₂ | CH |
| I-625 | | CH₃ | NH₂ | OCH₃ | CH |
| I-626 | | CH₃ | NHCH₃ | OCH₃ | CH |
| I-627 | | CH₃ | NHCH₃ | OCHF₂ | CH |
| I-631 | | CH₃ | OC₂H₅ | OC₂H₅ | CH |

TABLE 7-continued

| No. | A | R¹ | X¹ | X² | Z |
|---|---|---|---|---|---|
| I-632 | | CH₃ | OCF₂CHF₂ | SCH₃ | CH |
| I-633 | | CH₃ | OCH(CH₃)₂ | OCHF₂ | CH |
| I-634 | | CH₃ | OCH₂CF₃ | OCH₃ | CH |
| I-635 | | CH₃ | OCH₂CH₂F | OCH₃ | CH |
| I-636 | | CH₃ | OCH₂CHF₂ | OCH₃ | CH |
| I-637 | | CH₃ | OCH₃ | OC₂H₅ | CH |
| I-641 | | CH₃ | OCH₃ | OCF₂CHF₂ | CH |
| I-642 | | CH₃ | OCH₃ | OCF₂CHFCF₃ | CH |
| I-643 | | CH₃ | OCH₃ | OCH(CH₃)₂ | CH |
| I-644 | | CH₃ | OCH₃ | OCH₃ | CH |
| I-645 | | CH₃ | OCH₃ | SCH₃ | CH |
| I-646 | | CH₃ | OCH₃ | SCHF₂ | CH |
| I-647 | | CH₃ | OCHF₂ | OCH₂CF₃ | CH |
| I-651 | | CH₃ | OCHF₂ | OCH₂CH₃ | CH |
| I-652 | | CH₃ | OCHF₂ | OCH₂ | CH |
| I-653 | | CH₃ | OCHF₂ | OCHF₂ | CH |
| I-654 | | CH₃ | OCHF₂ | SCH₃ | CH |
| I-655 | | CH₃ | C₂H₅ | OCH₃ | N |
| I-656 | | CH₃ | C₂H₅ | SCH₃ | N |
| I-657 | | CH₃ | CF₃ | OCH₃ | N |
| I-661 | | CH₃ | CH(CH₃)₂ | CH₃ | N |
| I-662 | | CH₃ | CH(CH₃)₂ | Cl | N |
| I-663 | | CH₃ | CH(CH₃)₂ | OCH₃ | N |
| I-664 | | CH₃ | CH(CH₃)₂ | SCH₃ | N |
| I-665 | | CH₃ | CH₂CF₃ | CH₃ | N |
| I-666 | | CH₃ | CH₂F | CH₃ | N |
| I-667 | | CH₃ | CH₂F | OCH₃ | N |
| I-671 | | CH₃ | CH₂OCH₃ | CH₃ | N |
| I-672 | | CH₃ | CH₂OCH₃ | OCH₃ | N |
| I-673 | | CH₃ | CH₂SCH₃ | CH₃ | N |
| I-674 | | CH₃ | CH₂SCH₃ | Cl | N |
| I-675 | | CH₃ | CH₂SCH₃ | OC₂H₅ | N |
| I-676 | | CH₃ | CH₂SCH₃ | OCH₃ | N |
| I-677 | | CH₃ | CH₂SCH₃ | SCH₃ | N |
| I-681 | | CH₃ | CH₃ | CF₃ | N |
| I-682 | | CH₃ | CH₃ | CH₃ | N |
| I-683 | | CH₃ | CH₃ | Cl | N |
| I-684 | | CH₃ | CH₃ | F | N |
| I-685 | | CH₃ | CH₃ | H | N |
| I-686 | | CH₃ | CH₃ | OCH₂CF₃ | N |
| I-687 | | CH₃ | CH₃ | OCH₂CH₂F | N |
| I-691 | | CH₃ | CH₃ | OCH₂CHF₂ | N |
| I-692 | | CH₃ | CH₃ | OCH₃ | N |
| I-693 | | CH₃ | CH₃ | SCH₃ | N |
| I-694 | | CH₃ | CH₃ | SCHF₂ | N |
| I-695 | | CH₃ | CHF₂ | CH₃ | N |
| I-696 | | CH₃ | CHF₂ | OCH₃ | N |
| I-697 | | CH₃ | Cl | Cl | N |
| I-701 | | CH₃ | Cl | OCH(CH₃)₂ | N |
| I-702 | | CH₃ | Cl | OCH₂CF₃ | N |
| I-703 | | CH₃ | Cl | OCH₃ | N |
| I-704 | | CH₃ | Cl | SCH₃ | N |
| I-705 | | CH₃ | F | OCH₃ | N |
| I-706 | | CH₃ | H | NH(CH₃) | N |
| I-707 | | CH₃ | N(CH₃)₂ | OCH₃ | N |
| I-711 | | CH₃ | N(CH₃)₂ | SCHF₂ | N |
| I-712 | | CH₃ | NHCH₃ | OCH₃ | N |
| I-713 | | CH₃ | OC₂H₅ | OC₂H₅ | N |
| I-714 | | CH₃ | OCF₂CHF₂ | SCH₃ | N |
| I-715 | | CH₃ | OCF₂CHFBr | SCH₃ | N |
| I-716 | | CH₃ | OCF₂CHFCF₃ | SCH₃ | N |
| I-717 | | CH₃ | OCH(CH₃)₂ | OCH₃ | N |
| I-721 | | CH₃ | OCH(CH₃)₂ | SCH₃ | N |
| I-722 | | CH₃ | OCH(CH₃)CH₂CH₃ | OCH₃ | N |
| I-723 | | CH₃ | OCH₂CF₃ | OCF₂CHF₂ | N |
| I-724 | | CH₃ | OCH₂CF₃ | OCH₃ | N |
| I-725 | | CH₃ | OCH₂CHF₂ | OCH₃ | N |
| I-726 | | CH₃ | OCH₃ | OC₂H₅ | N |
| I-727 | | CH₃ | OCH₃ | OCF₂CHF₂ | N |
| I-731 | | CH₃ | OCH₃ | OCF₂CHFBr | N |
| I-732 | | CH₃ | OCH₃ | OCF₂CHFCF₃ | N |
| I-733 | | CH₃ | OCH₃ | OCF₂CHFCl | N |
| I-734 | | CH₃ | OCH₃ | OCH₃ | N |
| I-735 | | CH₃ | OCH₃ | OCHF₂ | N |
| I-736 | | CH₃ | OCH₃ | SCH(CH₃)₂ | N |
| I-737 | | CH₃ | OCH₃ | SCH₃ | N |
| I-738 | | CH₃ | OCH₃ | SCHF₂ | N |

TABLE 8

| No. | A | R¹ | X¹ | X² | Z |
|---|---|---|---|---|---|
| I-741 | In compounds | CH₃ | CH₃ | CH₃ | CH |
| I-742 | No. I-741– | | CH₃ | Cl | CH |
| I-743 | No. I-757, | | CH₃ | OCH₃ | CH |
| I-744 | the group A is | | Cl | Cl | CH |
| I-745 | A-3 | | Cl | OCH₃ | CH |
| I-746 | | | OCH₃ | OCH₃ | CH |
| I-747 | | | CH₃ | CH₃ | N |
| I-751 | | | CH₃ | Cl | N |
| I-752 | | | CH₃ | OCH₃ | N |
| I-753 | | | Cl | Cl | N |
| I-754 | | | Cl | OCH₃ | N |
| I-755 | | | N(CH₃)₂ | OCH₃ | N |
| I-756 | | | OCH₂CH₂F | OCH₃ | N |
| I-757 | | | OCH₃ | OCH₃ | N |

TABLE 9

| No. | A | R¹ | X¹ | X² | Z |
|---|---|---|---|---|---|
| I-761 | In compounds | H | CH₃ | CH₃ | CH |
| I-762 | No. I-761– | | CH₃ | Cl | CH |
| I-763 | No. I-777, | | CH₃ | OCH₃ | CH |
| I-764 | the group A is | | Cl | Cl | CH |
| I-765 | A-4(R⁴=H) | | Cl | OCH₃ | CH |
| I-766 | | | OCH₃ | OCH₃ | CH |
| I-767 | | | CH₃ | CH₃ | N |
| I-771 | | | CH₃ | Cl | N |
| I-772 | | | CH₃ | OCH₃ | N |
| I-773 | | | Cl | Cl | N |
| I-774 | | | Cl | OCH₃ | N |
| I-775 | | | N(CH₃)₂ | OCH₃ | N |
| I-776 | | | OCH₂CH₂F | OCH₃ | N |
| I-777 | | | OCH₃ | OCH₃ | N |

The N-(substituted amino)imide derivative of the above formula (I-a) can be synthesized by reacting an aminoazine derivative of the formula (V) with a halogenosulfonyl isocyanate of the formula (VI) to form an (azinylureylene) sulfonylhalide of the formula (III), followed by reacting it with an N-aminoimide derivative of the formula (II-a) without preferably isolating the intermediate, according to the following reaction formula.

$$Y^1SO_2N=C=O \qquad (VI)$$

$$NH_2-\underset{N}{\overset{N=\!\!\!\!\!-\!\!\!\!-X^1}{\diagup}}\!\!\!\!\!\!\!\!Z\!\!\!\!\!\!\!\!\diagdown_{X^2} \qquad (V)$$

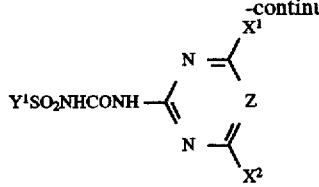

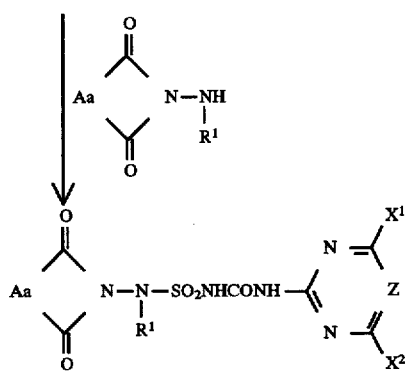

The N-(substituted amino)imide derivative of the above formula (I-b1) can also be synthesized by reacting a compound of the formula (I-b2) with a compound of the formula (IV) in a presence of a base to replace the hydrogen atom on N-amino group with $R^1b$ according to the following reaction formula:

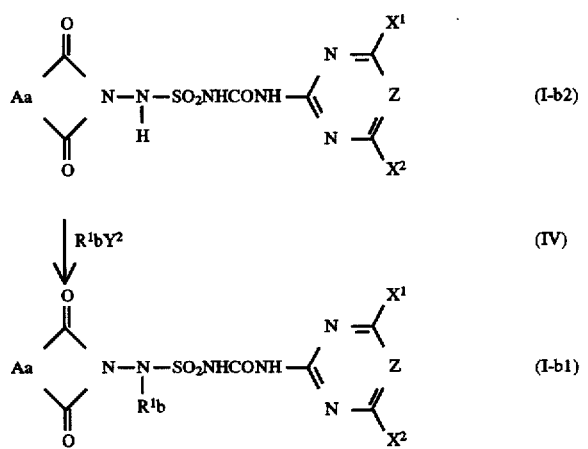

The compounds of the above formula (I-a) can be prepared by the following steps.

In the first step, an aminoazine derivative of the formula (V) is allowed to react with a halogenosulfonyl isocyanate of the formula (VI) in an inert organic solvent or diluent to form an (azinylureylene)sulfonylhalide of the formula (III), followed by reacting it with an N-aminoimide derivative of the formula (II-a) without preferably isolating the intermediate, according to the following reaction formula. If desired, the resultant compound of the formula (I-a) is allowed to react with alkali metal hydroxide or quaternary ammonium base to form a salt thereof.

The above reaction steps are preferred to carry out at a temperature in a range of from −78° C. to boiling point of the solvent and preferably from 0° C. to 40° C. in an inert organic solvent, for example, hydrocarbons such as benzene, toluene, xylene or cyclohexane, etc., chlorinated hydrocarbons such as methylene chloride, chloroform, carbon tetrachloride or chlorobenzene, ethers such as diethyl ether, dimethoxyethane, diethyleneglycol dimethyl ether, tetrahydrofuran, dioxane, and aprotic polar solvent such as acetonitrile or nitromethane.

In these reactions, it is preferred to use an organic tertiary amine, preferably pyridine or triethylamine, or an inorganic base such as carbonates of alkali metal as an acid acceptor.

If necessary, the compound of the formula (II-a) may be used in an excess amount so as to simultaneously react as an auxiliary base.

The reaction for replacing hydrogen atom of N-amino group on the imide group of the compound represented by the formula (I-b2) with the group $R^1b$ is carried out at a temperature in a range of from 0° C. to the boiling point of the solvent in the presence of an inorganic base such as sodium hydroxide or potassium carbonate in a solvent such as dioxane or dimethylacetamide. As a substitution reagent, a reagent which form the group $R^1b$ as an electrophilic cation can be used.

Examples of alkylating agent include dimethyl sulfate, methyl iodide, ethyl iodide, ethyl bromide and benzyl bromide, etc. Examples of acylating agent include acetyl chloride, propionyl chloride, butyryl chloride, acetic acid anhydride and propionic acid anhydride, etc. Examples of sulfonylating agent include methanesulfonyl chloride, ethanesulfonyl chloride and propanesulfonyl chloride, etc.

After completion of the reaction, the reaction mixture is added to an aqueous solution of diluted hydrochloric acid and the precipitate thus formed is collected by filtration. The precipitate is dried in air and then purified by column chromatography or by washing technique, whereby the N-(substituted amino)imide derivative of the formula (I-1b) can be obtained.

The compound of the formula (I) is possible to replace a hydrogen atom on the nitrogen atom of ureylene group with a suitable cation to form a salt. Examples of the salt generally include metal salts, particularly alkali metal salts and alkaline earth metal salts, and if necessary, ammonium salts and organic amine salts. The salts can be produced preferably at a temperature in a range of from 20° to 100° C. in a solvent such as water, alcohol or acetone. Preferred examples of the base for producing the salt of the compound (I) include alkali metal carbonates, ammonia and ethanolamine.

The starting material of the formula (V) can be synthesized by cyclization of a suitable guanidine derivative with a substituted 1,3-diketone. (The Chemistry of Heterocyclic Compounds., Vol.XVI (1962) and Supplement I (1970)).

The above compound can also be synthesized from an N-cyanoamidine derivative or an N-cyanoimidate derivative. (Refer to Journal of Organic Chemistry (J. Org. Chem.) 28., 1812–1821 (1963)).

Further, the above compound can be synthesized from cyanuric chloride. (For example, L. Rapoport: "The Chemistry of Heterocyclic Compounds", "s-triazines and Derivatives" (1959)).

Synthesis of the compound of the formula (II-a) can be carried out as follows. That is, the compound can be synthesized by reacting a 1,2-dicarboxylic acid of the formula (VIII) or mono- or diester thereof or, preferably, a 1,2-dicarboxylic acid anhydride of the formula (VII) with a hydrazine derivative of the formula (IX) in acetonitrile, lower alcohol, hydrochloric acid containing lower alcohol, or acetic acid, according to the following reaction formula.

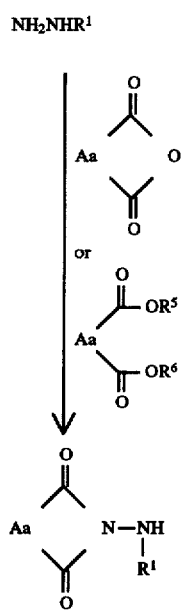

wherein R⁵ is hydrogen atom or $C_1$–$C_4$ alkyl group and R⁶ is $C_1$–$C_4$ alkyl group.

Specific examples of compounds represented by the formula (II-a) used as the above described intermediates are shown in Table 10.

TABLE 10

| Compound No. | A | R¹ |
|---|---|---|
| II-1 | A-1(R²=R³=CH³) | H |
| II-2 | A-1(R²=R³=CH³) | CH³ |
| II-3 | A-1(R²=R³=CH³) | CH₂Ph |
| II-4 | A-2 | H |
| II-5 | A-2 | CH³ |
| II-6 | A-2 | CH₂Ph |
| II-7 | A-3 | H |
| II-8 | A-3 | CH³ |
| II-9 | A-3 | CH₂Ph |
| II-10 | A-4(R⁴=H) | H |
| II-11 | A-4(R⁴=H) | CH³ |
| II-12 | A-4(R⁴=H) | CH₂Ph |

The N-(substituted amino)imide derivative of the above formula (I) according to the present invention which is novel compound exhibits a certain herbicidal effect in a low dosage, and has a selectivity between crops and weeds. Accordingly, a herbicidal composition comprising this compound as an active ingredient is suitable, e.g., for controlling monocotyledonous and dicotyledonous weed in important crops, such as wheat, rice, corn, soybean, cotton, beet, potato and tomato, before or after germination.

Examples of dicotyledonous weeds which can be prevented by the herbicidal composition of the present invention include weeds belonging to Amaranthus, Bidens, Stellaria, Abutilon, Convolvulus, Matricaria, Galium, Lindernia, and the like.

Examples of monocotyledonous weeds include weeds belonging to Echinochloa, Setaria, Digitaria, Arena, Cyperus, Alisma, Monochoria, and the like.

The herbicidal composition according to the present invention may be applied in areas such as farming areas, inclusive of farms, paddy fields and orchards, as well as non-farming areas, inclusive of grounds and industrial sites.

The compound of the present invention can be utilized as is, but it is generally used in various forms of preparations, such as dust, wettable powder, granule, emulsion, etc., together with a preparation adjuvant.

In this case, a preparation is prepared so that one or more compounds of the present invention are contained in an amount of 0.1 to 95% by weight, preferably 0.5 to 90% by weight, and particularly 2 to 70% by weight.

Examples of carriers, diluents, and surfactant, which can be used as the preparation adjuvant, include talc, kaolin, bentonite, diatom earth, white carbon, clay, and the like. As liquid diluents, water, xylene, toluene, chlorobenzene, cyclohexane, cyclohexanone, dimethylsulfoxide, dimethylformamide, alcohols, and the like can be exemplified.

Surfactants are preferably used depending upon their effects. Examples of emulsifiers are polyoxyethylene alkylaryl ether, polyoxyethylene sorbitan monolaurate, etc.; examples of dispersants are lignin sulfonates, dibutylnaphthalene sulfonate, etc.; and examples of wetting agents are alkylsulfonates, alkylphenyl sulfonates, etc.

The above-mentioned preparation can be roughly divided into one which is used as is and one which is used by diluting with a diluent such as water. In the latter case, the concentration of the compound of the present invention preferably ranges from 0.001 to 1.0%.

The amount of the compound of the present invention used is in a range of from 0.01 kg to 10 kg, preferably 0.05 kg to 5 kg, per 1 ha.

Since the concentration and the amount used vary with the form of preparation, the period of usage, the manners of usage, the sites of the usage, the intended crops, and other factors, these values can, of course, be changed in spite of the above ranges. Moreover, the compound of the present invention can be used in combination with other active ingredients, such as fungicides, bactericides, miticides and herbicides.

EXAMPLES

The present invention will now be described in detail by referring to Synthesis Examples of the N-(substituted amino)imide derivatives represented by the formula (I), Preparation Examples and Test Example. The present invention is not limited to the following Synthesis Examples, Preparation examples and Test Example unless departing from the scope of the present invention. Synthesis Example 1

Synthesis of N-(4,6-dimethoxy-2-pyrimidinyl)-N'-{[(2,3-dimethylmaleimido)amino]sulfonyl}urea (I-74)

To a solution of chlorosulfonylisocyanate (0.94 g; 6.5× 1.02 mM) dissolved in 10 ml of dichloromethane at –70° C. was added dropwise 20 ml of a solution of 2-amino-4,6-dimethoxypyrimidine (1.0 g, 6.5 mM) in dichloromethane. Then, the temperature of the reaction system was controlled over 1 hour so as to be near 0° C. After cooling again to –70° C., a solution of N-2,3-dimethylmaleimide (1.82 g; 6.5×22 mM) in 10 ml of dichloromethane was added dropwise.

The mixture was then stirred over a night while the temperature was elevated to room temperature. Thereafter, the solvent in the reaction mixture was distilled at room temperature, and water was added to the resultant residue. The precipitated solid was filtered off. The resultant product was washed with hot acetonitrile to obtain the target product.

Yield 0.52 g (52%); HPLC purity 99.7% (254 nm); White solid; m.p. 190° C. (decomposition)

IR(KBr cm⁻¹): 3292 1746 1704 1614 1578 1500 1455 1365 1200 1173

$^1$H-NMR(60 MHz; d$_6$-DMSO, δ)=1.85(6H,s, maleimide ring CH$_{3\times 2}$) 3.76(6H,s, pyrimidine ring OCH$_{3\times 2}$) 5.8(1H,s, pyrimidine ring H) 10.5(1H,s,NH) 11.0(1H,s,NH) 12.3(1H, s,NH)

Synthesis Example 2

Synthesis of N-(4,6-dimethoxy-2-pyrimidinyl)-N'-{[(2,3-dimethylmaleimido)(methyl)amino]sulfonyl}urea (I-244)

To a solution of chlorosulfonylisocyanate (0.48 g; 3.2×1.05 mM) dissolved in 10 ml of dried dichloromethane at −70° C. was added dropwise 20 ml of a solution of N-(methylamino)-2,3-dimethylmaleimide (II-2)(0.5 g, 3.2 mM) in dichloromethane, followed by adding dropwise 10 ml of a solution of triethylamine (0.42 g, 3.2×1.1mM). The reaction mixture was stirred for 20 hours while the temperature was raised to room temperature. Thereafter, the solvent in the reaction mixture was distilled, and water was added to the resultant residue. The precipitated solid was filtered off. The resultant solid was washed with a small amount of hot ethyl acetate and purified by chromatography.

Yield 0.737 g, (55%); purity 98.4%(254 nm); white solid; m.p. 169°–171° C.;

IR (KBr cm$^{-1}$): 1742 1710 1610 1582 1506 1456 1378 1360 1222 1162;

$^1$H-NMR (60 MHz; CDCl$_3$, δ): 1.97(6H,s, maleimide ring CH$_{3\times 2}$) 3.49(3H,s, N—CH$_3$) 3.86(6H,s, pyrimidine ring OCH$_3$×2) 5.78(1H,s, pyrimidine ring H) 7.63(1H,bs,NH) 12.6(1H,bs, NH).

Synthesis Example 3

Synthesis of N{[(benzyl)(2,3-dimethlmaleimido)-amino]sulfonyl}-N'-(4,6-dimethoxy-2-pyrimidinyl)urea (I-346)

The target compound was synthesized by ureylenesulfonylation of N-(benzylamino)-2,3-dimethylmaleimide (II-3) synthesized according to the below-mentioned Reference Synthesis Example 2, by the same manner as in Synthesis Example 1.

Yield 0.98 g (74.2%); HPLC purity 95.4%; white solid; m.p. 171°–173° C.

IR (KBr cm–1): 1743 1713 1611 1584 1461 1362

$^1$H-NMR (60 MHz; CDCl$_3$, δ): 1.8(6H,s, maleimide ring CH$_3$×2) 3.8(6H,s, pyrimidine ring OCH$_3$×2) 5.05(2H,s, N-CH$_2$) 5.66(1H,s, pyrimidine ring H) 7.1–7.3(5H,m, benzene ring H) 7.63(1H,br,NH) 12.5(1H,br,NH).

Synthesis Example 4

Synthesis of N-(4,6-dimethoxy-2-pyrimidinyl)-N'-{[(acetyl)(2,3-dimethylmaleimido)amino]sulfonyl}urea (I-366)

N-(4,6-dimethoxypyrimidin-2-yl)-N'-{[(2,3-dimethylmaleimido)amino]sulfonyl}urea (I-74)(0.78 g, 1.95 mmol) synthesized according to synthesis Example 1 was dissolved in 20 ml of dried dimethylformamide. To the solution was added under cooling with ice-water 60% sodium hydride (0.078 g, 1.95 mmol). After conclusion of foaming, acetic acid anhydride (0.2 g, 1.95 mmol) was added and stirred at room temperature for 20 hours. The reaction mixture was then poured into ice-water, and the solid precipitate was filtered, washed with water and dried.

Yield 0.48 g (56.6%); HPLC purity (254 nm)98.4%; white solid; m.p. 167°–168° C. (decomposition);

IR (KBr cm$^{-1}$): 3272 2932 1748 1718 1620 1584 1512 1454 1378 1228 1174;

$^1$H-NMR (60 MHz: d$_6$-DMSO, δ): 1.93(6H,s, maleimide ring CH$_{3\times 2}$) 2.5(3H,s,COCH$_3$) 3.73(1H,s,NH) 3.81(6H,s, pyrimidine ring OCH$_3$×2) 10.7(1H,s,NH);

MS[DI]: m/z 181(dimethylimide —NCOCH$_{3,2}$) 43(100)

Synthesis Example 5

Synthesis of N-(4,6-dimethoxy-2-pyrimidinyl)-N'-{[(2,3-dimethylmaleimido)(methylsulfonyl)amino]-sulfonyl}urea (I-386)

N-(4,6-dimethoxypyrimidin-2-yl)-N'-{[(2,3-dimethylmaleimido)amino]sulfonyl}urea (I-74)(0.32 g, 0.81 mM) synthesized according to synthesis Example 1 was dissolved in 20 ml of dried dimethylformamide. To the solution was added under cooling with ice-water 60% sodium hydride (0.0324 g, 0.81 mM). After conclusion of foaming, methylsulfonyl chloride (0.093 g, 0.81 mM) was added and stirred at room temperature for 17 hours. The reaction mixture was then poured into water, and extracted with ethyl acetate. The resultant organic layer was washed with diluted hydrochloric acid and saturated saline solution. After ethyl acetate was distilled away, the product was purified by chromatography.

Yield 0.044 g (11.4%); HPLC purity (254 nm) 95.0%; white solid; m.p. 160°–162° C. (decomposition)

IR (KBr cm): 1770 1635 1380 1200;

$^1$H-NMR (60 MHz; CDCl$_3$, δ): 1.98(6H,s, maleimide ring CH$_3$×2) 3.45(3H,s, SO$_2$CH$_3$) 3.85(6H,S, pyrimidine ring OCH$_3$×2) 5.68(1H,s, pyrimidine ring H) 7.38(1H,br, NH) the others are indistinct.

Synthesis Example 6

Synthesis of N-(4,6-dimethoxy-2-pyrimidinyl)-N'-{[(maleimido)(methyl)amino]sulfonyl}urea (I-474)

N-(4,6-dimethoxy-2-pyrimidinyl)-N'-{[(exo-3,6-epoxy-1,2,3,6-tetrahydrophthalimido)(methyl)amino]sulfonyl}urea (I-644) (0.4 g, 0.88 mmol) synthesized according to the below-mentioned Synthesis Example 7 was heated at 140° C. for 1 hour in the absence of solvent. After cooling, 20 ml of acetonitrile was added. After stirred, the mixture was filtered to obtain 0.16 g of a solid product. It was dissolved in 5 ml of dimethylformamide and reprecipitated by adding 10 ml of water. The solid precipitate was filtered, washed with water and dried.

Yield 0.048 g (14.1%); HPLC purity (254 nm) 91%; white solid; m.p. 197° C. (decomposition)

IR (KBr cm$^{-1}$): 1743 1716 1617 1578 1452 1377 1161

$^1$H-NMR (60 MHz: d$_6$-DMSO, δ): 3.3(3H,S, N—CH$_3$) 3.73(6H,S, pyrimidine ring OCH$_3$×2) 5.8(1H,S, pyrimidine ring H) 7.0(2H,S, maleimide ring H×2) 10.4(1H,S,NH) 12.3(1H,brs, NH)

LC/MS[DI]: m/z 387(M+1)

Synthesis Example 7

Synthesis of N-(4,6-dimethoxy-2-pyrimidinyl)-N'-{[(exo-3,6-epoxy-1,2,3,6-tetrahydrophthalimido)(methyl)-amino]sulfonyl}urea (I-644)

The target compound was synthesized by ureylenesulfonylation of exo-3,6-epoxy-N-(methylamino)-1,2,3,6-tetrahydrophthalimide (II-5) synthesized according to the below-mentioned Reference Synthesis Example 3, by the same manner as in Synthesis Example 1.

Yield 0.55 g (59.1%); HPLC purity (254 nm) 97.4%; white solid; m.p. begin to fuse at 177° C. and decompose at 186° C.;

IR (KBr cm$^{-1}$): 3262 3022 1797 1746 1614 1575 1455 1368

$^1$H-NMR (60 MHz; d$_6$-DMSO, δ): 2.8(2H,m, epoxytetrahydrophthalimide ring H) 3.3(3H,s, NCH$_3$) 3.78(6H,s, pyrimidine ring OCH$_3$×2) 4.78–5.18(2H, epoxytetrahydrophthalimide ring H) 5.84(1H,s, pyrimidine ring H) 10.5(1H, bs,NH) 12.5(1H,bs,NH)

Synthesis Example 8

Synthesis of N-(4,6-dimethoxy-2-pyrimidinyl)-N'-{[(methyl)(cis-5-norbornene-end-2,3-dicarboxyimido)amino]sulfonyl}urea (I-746)

The target compound was synthesized by ureylenesulfonylation of N-(methylamino)-cis-5-norbornene-endo-2,3-dicarboximide (II-8) synthesized according to the below-mentioned Reference Synthesis Example 4, by the same manner as in Synthesis Example 1.

Yield 0.42 g (6.0%); HPLC purity (254 nm) 95.4%; white solid; m.p.170°–175° C. (decomposition at 193° C.)

IR (KBr cm$^{-1}$): 1743 1611 1455 1362 1197 1173

$^1$H-NMR (60 MHz; d$_6$-DMSO, δ): 1.46(2H,m, norbornene ring H) 3.06×3.41(7H,m, NCH$_3$, norbornene ring H×4) 3.76, 3.8(each 3H,s, pyrimidine ring OCH$_3$×2) 5.77–6.1(3H,m, norbornene ring H×2, pyrimidine ring H) 10.46(1H,bs,NH) 12.2(1H,bs,NH)

Synthesis Example 9

Synthesis of N-(4,6-dimethoxy-2-pyrimidinyl)-N'-[(phthalimidoamino)sulfonyl]urea (I-766)

The target compound was synthesized by ureylenesulfonylation of N-aminophthalimide according to the same manner as in Synthesis Example 1.

Yield 0.49 g (60%); HPLC (254 nm) purity 99.6%; white solid; m.p. 183°–185° C. (decomposition);

IR (KBr cm$^{-1}$); 3228 1798 1732 1612 1586 1454 1364 1200

$^1$H-NMR (60 MHz; d$_6$-DMSO, δ): 3.75(6H,s, pyrimidine ring OCH$_3$×2) 5.83(1H,s, pyrimidine ring H) 7.86(4H,s, benzene ring H) 10.5(1H,s, NH) 11.26(1h,bs,NH) 12.3(1H, bs,NH)

Reference Synthesis Example 1

Synthesis of N-(methylamino)-2,3-dimethylmaleimide [(II-2) intermediate for Synthesis Example 2]

2,3-Dimethylmaleic acid anhydride (3.5 g, 28 mM) was suspended in 50 ml of ethyl alcohol. To the dispersion was added methylhydrazine (1.28 g, 27.7 mM). After addition, the mixture was stirred at 70° C. for 3 hours. After ethanol was distilled away, the target compound was separated by chromatography from the reaction mixture.

Yield 0.7 g (16.4%); HPLC purity 97.8 %; light green solid; m.p. 61°–62° C.;

$^1$H-NMR (60 MHz; CDCl$_3$,δ): 1.93(6H,s; CH$_3$×2) 2.66 (3H,d,J=5 Hz;NHCH$_3$) 4.22(1H,bq,J=5 Hz; NH)

Reference Synthesis Example 2

Synthesis of N-(benzylamino)-2,3-dimethylmaleimide [(II-3) intermediate for Synthesis Example 3]

The target compound was synthesized by reacting benzylhydrazine with 2,3-dimethylmaleic acid anhydride according to the same manner as in Reference Synthesis Example 1.

Yield 1.28 g (23.3%); HPLC purity 95.8%; light yellow solid; m.p. 95°–97° C.;

IR (KBr cm$^{-1}$): 3274 1779 1713 1491 1458 1398 1095 753

$^1$H-NMR (60 MHz; CDCl$_3$, δ): 1.9(6H,S: maleimide ring CH$_3$×2) 4.0(2H,bs: NHCH$_2$) 4.36(1H,bs:NH) 7.06–7.46 (5H,m benzene ring H)

Reference Synthesis Example 3

Synthesis of exo-3,6-epoxy-N-(methylamino)-1,2,3,6-tetrahydrophthalimide [(II-5) intermediate for Synthesis Example 7]

Exo-3,6-epoxy-1,2,3,6-tetrahydrophthalic acid anhydride (3.5 g, 21 mM) was dissolved in 50 ml of acetonitrile. To the solution was added dropwise methylhydrazine (0.97 g, 21 mM) in 5 ml of acetonitrile at room temperature. The mixture was refluxed with heat to 70° C. for 4 hours. After cooled, the precipitated solid was filtered off and the filtrate was condensed. The residue was purified with column chromatography on silica gel (elution solvent: ethyl acetate/ n-hexane=1/1) to obtain the target compound as white solid.

Yield 0.69 g (16.9%); white solid; m.p. 155° C. (decomposition);

IR (KBr cm$^{-1}$): 3316 1782 1713 1530 1248 1179 1014 876 717

$^1$H-NMR (60 MHz; CDCl$_3$, δ): 2.62(3H,S, N—CH$_3$) 2.73(2H,s, epoxytetrahydrophthalimide ring H) 4.23(1H,br, NH) 5.18(2H,s, epoxytetrahydrophthalimide ring H) 6.4 (2H,s, epoxytetrahydrophthalimide ring H)

Reference Synthesis Example 4

Synthesis of N-(methylamino)-cis-5-norbornene-endo-2,3-dicarboximide [(II-8) intermediate for Synthesis Example 8]

The target compound was synthesized by reacting cis-5-norbornene-endo-2,3-dicarboxylic acid anhydride with methyl hydrazine according to the same manner as in Reference Synthesis Example 3.

Yield 0.93 g (22.7%); white solid; m.p. 126°–130° C.;

IR (KBr cm$^{-1}$): 3316 3004 1767 1713 1509 1389 1242 1173 1134 726

$^1$H-NMR (60 MHz; CDCl$_3$, δ): 1.47(1H,m, norbornene ring H) 1.74(1H,m, norbornene ring H) 2.53(3H,s, NCH$_3$) 3.08–3.53(4H,m, norbornene ring H) 4.26(1H,br,NH) 6.03 (2H,m, norbornene ring H)

In the above Synthesis Examples and Reference Synthesis Examples symbols in NMR have the following meanings:

s (single), d (doublet), t (triplet), q (quartet), m (multiplet), dd (double doublet), and br (broad).

Formulation Examples and Test Examples will hereinafter be described. It should be borne in mind that the vehicles (diluents), adjuvants, their mixing ratio and effective components can vary in wide ranges respectively. In these examples, all "parts" are by weight. Formulation Example 1 (Wettable Powder)

| | |
|---|---|
| Compound (I-386) | 50 parts |
| Salt of ligninsulfonic acid | 5 parts |
| Salt of alkylsulfonic acid | 3 parts |
| Diatomaceous earth | 42 parts |

The above ingredients are mixed and ground into a wettable powder. For application, it is diluted with water.

Formulation Example 2 (Emulsion)

| | |
|---|---|
| Compound (I-746) | 25 parts |
| Xylene | 65 parts |
| Polyoxyethylene alkylaryl ether | 10 parts |

The above ingredients are mixed intimately into an emulsion. For application, it is diluted with water. Formulation Example 3 (Granule)

| Compound (I-244) | 8 parts |
|---|---|
| Bentonite | 40 parts |
| Clay | 45 parts |
| Ligninsulfonic acid | 7 parts |

The above ingredients are mixed intimately. After the addition of water, the mixture was kneaded and then formed into granules by an extruding granulator. Test 1 Test on herbicidal activity by foliar application Herbicidal solutions of each test compound, which had been prepared by dissolving at predetermined concentrations such as wettable powder of the test compound as that described in the above formulation example, and sprayed at a dosage of 1000 g/ha over foliar parts of Amaranthus retroflexus, Bidenes pilosa, Sinapis arvensis, Stellaria media, Cassia obtusifolia, Solanum nigrum, Abutilon theophrasti, Convolvulus arvensis, Matricaria chamomilla, Galium aparine, Veronica hederaeforia, Setaria viridis, Echinochloa frumentaceum, Arena fatua, Digitaria adscendens (which had been allowed to grow individually to 1–2 leaf stage). Fourteen days later after spraying of the test compound, its herbicidal activity was evaluated in accordance with the below-described 3-stage system. The results are summarized in Table II. Growth inhibition rate 1: less than 30%; 2: 30% to less than 70%; 3: 70% or more

TABLE II

| | Compound (I) 1000 g/ha | | | | | | | | |
|---|---|---|---|---|---|---|---|---|---|
| Feed | 74 | 244 | 346 | 366 | 386 | 474 | 644 | 746 | 766 |
| A.r. | 3 | 3 | 1 | 3 | 2 | 3 | 2 | 2 | 2 |
| B.p. | 2 | 3 | 1 | 2 | 2 | 3 | 2 | 2 | 1 |
| S.a. | 3 | 3 | 3 | 3 | 3 | 3 | 3 | 3 | 1 |
| S.m. | 1 | 3 | 1 | 1 | 2 | 3 | 1 | 3 | 1 |
| C.f. | 1 | 3 | 1 | 3 | 2 | 3 | 1 | 1 | 1 |
| S.n. | 3 | 3 | 1 | 3 | 2 | 3 | 1 | 2 | 1 |
| A.t. | 3 | 3 | 1 | 2 | 1 | 2 | 1 | 1 | 1 |
| C.a. | 3 | 3 | 1 | 3 | 2 | 3 | 1 | 1 | 1 |
| M.c. | 3 | 3 | 1 | 1 | 1 | 3 | 1 | 1 | 1 |
| G.a. | 2 | 3 | 1 | 3 | 3 | 3 | 1 | 1 | 1 |
| V.h. | 2 | 3 | 1 | 2 | 3 | 1 | 1 | 1 | 1 |
| S.v. | 1 | 3 | 1 | 1 | 3 | 1 | 1 | 1 | 1 |
| E.f. | 1 | 3 | 1 | 1 | 3 | 2 | 1 | 1 | 1 |
| A.f. | 1 | 2 | 1 | 1 | 2 | 2 | 1 | 1 | 1 |
| D.a. | 1 | 1 | 1 | 1 | 1 | 2 | 1 | 1 | 1 |

A.r.: Amaranthus retroflexus
B.p.: Bidenes pilosa
S.a.: Sinapis arvensis
S.m.: Stellaria media
C.f.: Cassia obtusifolia
S.n.: Solanum nigrum
A.t.: Abutilon theophrasti
C.a.: Convolvulus arvensis
N.c.: Natricaria chamomilla
G.a.: Galium aparine
V.h.: Veronica hederaeforia
S.v.: Setaria viridis
E.f.: Echinochloa frumentaceum
A.f.: Avens fetua
D.a.: Digitaria adscendens

We claim:

1. An N-(substituted amino)imide derivative represented by the formula (I):

(I)

wherein, $R^1$ is a hydrogen atom, $C_1$–$C_4$ alkyl group, $C_7$–$C_9$ aralkyl group, $C_1$–$C_4$ haloalkyl group, ($C_1$–$C_4$ alkyl) carbonyl group or a ($C_1$–$C_4$ alkyl) sulfonyl group;

A represents a structure selected from the group consisting of the following formulas (1), (2), (3) and (4)

(1)

(2)

(3)

(4)

wherein $R^2$ and $R^3$ in the formula (1) are independently a hydrogen atom or a $C_1$–$C_4$ alkyl group, but not $R^2$=$R^3$=H, $X^1$ and $X^2$ are independently a hydrogen atom, a halogen atom, $C_1$–$C_4$ alkyl group, $C_1$–$C_4$ alkoxy group, $C_1$–$C_4$ alkylthio group, $C_1$–$C_4$ haloalkyl group, $C_1$–$C_4$ haloalkoxy group, $C_1$–$C_4$ haloalkylthio group, $C_2$–$C_4$ alkoxyalkyl group, $C_2$–$C_4$ thioalkoxyalkyl group, or $NR^7R^8$, wherein $R^7$ and $R^8$ are independently a hydrogen atom, $C_1$–$C_4$ alkyl group or $C_1$–$C_4$ alkoxy group; and Z is a nitrogen atom or CH.

2. The N-(substituted amino)imide derivative according to claim 1, wherein Z is CH and A is of the formula (1) $R^2$=$R^3$=methyl, formula (2), formula (3) or formula (4).

3. The N-(substituted amino)imide derivative according to claim 1, wherein Z is N, and A is of the formula (1) where $R^2$=$R^3$=methyl, formula (2), formula (3) or formula (4).

4. A process for preparation of an N-(substituted amino) imide derivative represented by the formula (I-a), which comprises reacting an N-aminoimide derivative of the formula (II-a) with an (azinylureylene)sulfonyl halide of the formula (III):

(I-a)

-continued

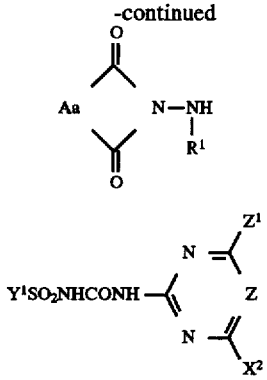
(II-a)

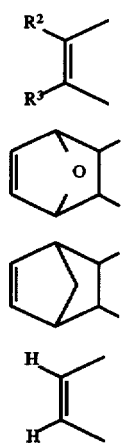
(III)

wherein Aa is a structure selected from the group consisting of the following formulas (1), (2), (3) and (4)

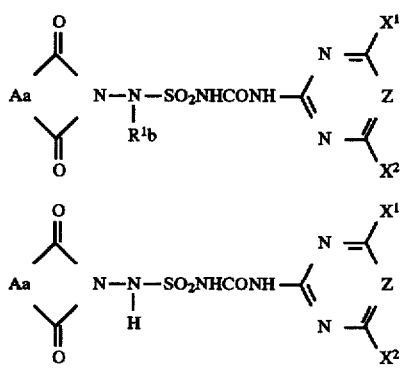

wherein $R^2$ and $R^3$ in the formula (1) are independently a hydrogen atom or a $C_1$–$C_4$ alkyl group, but not $R^2=R^3=H$; $X^1$ and $X^2$ are independently a hydrogen atom, a halogen atom, $C_1$–$C_4$ alkyl group, $C_1$–$C_4$ alkoxy group, $C_1$–$C_4$ alkylthio group, $C_1$–$C_4$ haloalkyl group, $C_1$–$C_4$ haloalkoxy group, $C_1$–$C_4$ haloalkylthio group, $C_1$–$C_4$ alkoxyalkyl group, $C_2$–$C_4$ thioalkoxyalkyl group or $NR^7R^8$, wherein $R^7$ and $R^8$ are independently a hydrogen atom, $C_1$–$C_4$ alkyl group or $C_1$–$C_4$ alkoxy group; Z is a nitrogen atom or CH; and $Y^1$ is a halogen atom.

5. A process for preparation of an N-(substituted amino) imide derivative represented by the formula (I-b1), which comprises reacting an N-(substituted amino)imide derivative of the formula (I-b2) with a compound represented by the formula (IV) in the presence of a base to replace the hydrogen atom on N-amino group with $R^1b$:

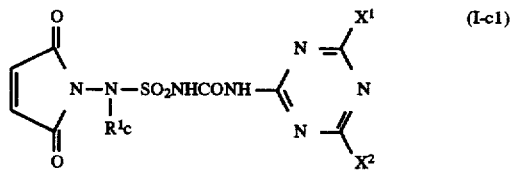
(I-b1)

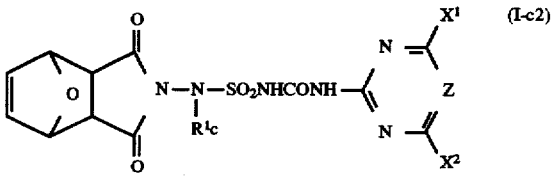
(I-b2)

$R^1bY^2$ (IV)

wherein Aa is a structure selected from the group consisting of the following formulas (1), (2) or (3)

(1)

(2)

(3)

wherein $R^2$ and $R^3$ in the formula (1) are independently a hydrogen atom or a $C_1$–$C_4$ alkyl group, but not $R^2=R^3=H$; $X^1$ and $X^2$ are independently a hydrogen atom, a halogen atom, $C_1$–$C_4$ alkyl group, $C_1$–$C_4$ alkoxy group, $C_1$–$C_4$ alkylthio group, $C_1$–$C_4$ haloalkyl group, $C_1$–$C_4$ haloalkoxy group, $C_1$–$C_4$ haloalkylthio group, $C_2$–$C_4$ alkoxyalkyl group, $C_2$–$C_4$ thioalkoxyalkyl group or $NR^7R^8$, wherein $R^7$ and $R^8$ are independently hydrogen atom, $C_1$–$C_4$ alkyl group or $C_1$–$C_4$ alkoxy group; Z is a nitrogen atom or CH; $R^1b$ is $C_1$–$C_4$ alkyl group, $C_7$–$C_9$ aralkyl group, $C_1$–$C_4$ haloalkyl group, ($C_1$–$C_4$ alkyl)carbonyl group or ($C_1$–$C_4$ alkyl)sulfonyl group; and $Y^2$ is a halogen atom or [$C_1$–$C_4$ alkyl]carbonyl]oxy group.

6. A process for preparation of an N-(substituted amino) imide derivative of the formula (I-c1), which comprises pyrolysis of an N-(substituted amino)imide derivative of the formula (i-c2):

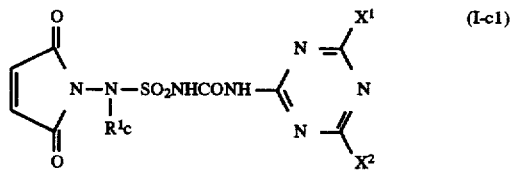
(I-c1)

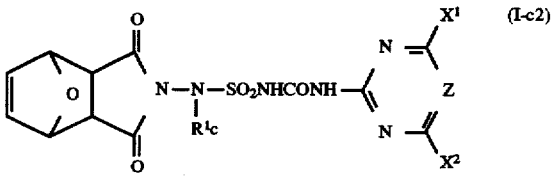
(I-c2)

wherein $R^1c$ is $C_1$–$C_4$ alkyl group, $C_7$–$C_9$ aralkyl group or $C_1$–$C_4$ haloalkyl group, $X^1$ and $X^2$ are independently a hydrogen atom, a halogen atom, $C_1$–$C_4$ alkyl group, $C_1$–$C_4$ alkoxy group, $C_1$–$C_4$ alkylthio group, $C_1$–$C_4$ haloalkyl group, $C_1$–$C_4$ haloalkoxy group, $C_1$–$C_4$ haloalkylthio group, $C_2$–$C_4$ alkoxyalkyl group, $C_2$–$C_4$ thioalkoxyalkyl group or $NR^7R^8$, wherein $R^7$ and $R^8$ are independently a hydrogen atom, $C_1$–$C_4$ alkyl group or $C_1$–$C_4$ alkoxy group; and Z is a nitrogen atom or CH.

7. A herbicidal composition which comprises a herbicidally effective amount of an N-(substituted amino)imide derivative represented by the formula (I) as an active ingredient and a carrier therefor,

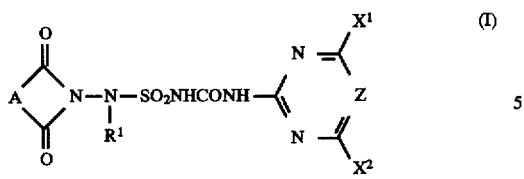

wherein, $R^1$ is a hydrogen atom, $C_7$–$C_9$ alkyl group, $C_1$–$C_4$ aralkyl group, $C_1$–$C_4$ haloalkyl group, ($C_1$–$C_4$ alkyl) carbonyl group or ($C_1$–$C_4$ alkyl)sulfonyl group;

A represents a structure selected from the group consisting of the following formulas (1), (2), (3) and (4)

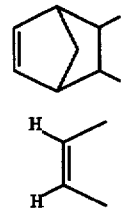

wherein $R^2$ and $R^3$ in the (1) are independently a hydrogen atom or a $C_1$–$C_4$ alkyl group, but not $R^2$=$R^3$=H; $X^1$ and $X^2$ are independently a hydrogen atom, a halogen atom, a $C_1$–$C_4$ alkyl group, $C_1$–$C_4$ alkoxy group, $C_1$–$C_4$ alkylthio group, $C_1$–$C_4$ haloalkyl group, $C_1$–$C_4$ haloalkoxy group, $C_1$–$C_4$ haloalkylthio group, $C_2$–$C_4$ alkoxyalkyl group, $C_2$–$C_4$ thioalkoxyalkyl group or $NR^7$; $R^8$, wherein $R^7$ and $R^8$ are independently a hydrogen atom, $C_1$–$C_4$ alkyl group or $C_1$–$C_4$ alkoxy group; and Z is a nitrogen atom or CH.

* * * * *